United States Patent
Clausen et al.

(10) Patent No.: US 10,585,484 B2
(45) Date of Patent: Mar. 10, 2020

(54) APPARATUS, SYSTEM, AND METHOD FOR TRANSFERRING DATA FROM A TERMINAL TO AN ELECTROMYOGRAPHY (EMG) DEVICE

(71) Applicant: Samsung Electronics Co., Ltd., Suwon-si, Gyeonggi-do (KR)

(72) Inventors: William Stryker Clausen, Kirkland, WA (US); Ashish Verma, Issaquah, WA (US)

(73) Assignee: Samsung Electronics Co., Ltd., Suwon-si (KR)

( * ) Notice: Subject to any disclaimer, the term of this patent is extended or adjusted under 35 U.S.C. 154(b) by 792 days.

(21) Appl. No.: 14/143,733

(22) Filed: Dec. 30, 2013

(65) Prior Publication Data

US 2015/0185853 A1    Jul. 2, 2015

(51) Int. Cl.
| | |
|---|---|
| *G06F 3/01* | (2006.01) |
| *A61B 5/0488* | (2006.01) |
| *A61B 5/00* | (2006.01) |
| *G16H 40/63* | (2018.01) |

(52) U.S. Cl.
CPC ............ *G06F 3/017* (2013.01); *A61B 5/0004* (2013.01); *A61B 5/0488* (2013.01); *A61B 5/6824* (2013.01); *A61B 5/742* (2013.01); *A61B 5/7475* (2013.01); *G06F 3/015* (2013.01); *G16H 40/63* (2018.01); *A61B 5/002* (2013.01)

(58) Field of Classification Search
CPC .................................................. A61B 5/04004
See application file for complete search history.

(56) References Cited

U.S. PATENT DOCUMENTS

| | | | |
|---|---|---|---|
| 7,596,393 B2 | 9/2009 | Jung et al. | |
| 8,292,833 B2 | 10/2012 | Son et al. | |
| 2004/0068409 A1* | 4/2004 | Tanaka | B25J 9/1656 704/272 |
| 2004/0236850 A1* | 11/2004 | Krumm | H04L 29/06 709/224 |
| 2009/0326406 A1* | 12/2009 | Tan | G06F 3/015 600/546 |
| 2010/0156676 A1* | 6/2010 | Mooring | G06F 3/017 341/20 |

(Continued)

FOREIGN PATENT DOCUMENTS

| | | |
|---|---|---|
| KR | 20090097330 A | 9/2009 |
| KR | 20100074461 A | 7/2010 |

(Continued)

OTHER PUBLICATIONS

Myo, getmyo.com Dec. 12, 2013.

*Primary Examiner* — Patrick Fernandes

(57) ABSTRACT

An apparatus, a system, and a method for transferring data from a terminal to an Electromyography (EMG) device are provided. The method includes detecting a user motion, determining whether the user motion corresponds to a motion associated with requesting data to be transferred from the source terminal to the EMG device, and if the user motion corresponds to a motion associated with requesting data to be transferred to from the source terminal to the EMG device, transmitting to the source terminal a request for the data according to the user motion.

27 Claims, 11 Drawing Sheets

(56) References Cited

U.S. PATENT DOCUMENTS

2011/0221669 A1* 9/2011 Shams ................. G02B 27/017
                                                  345/156
2012/0188158 A1   7/2012 Tan et al.
2013/0265229 A1* 10/2013 Forutanpour ........... G06F 3/014
                                                  345/158
2014/0282269 A1*  9/2014 Strutt ................. G06F 3/04883
                                                  715/863

FOREIGN PATENT DOCUMENTS

| KR | 10-2011-0040165 A | 4/2011 |
|----|-------------------|--------|
| KR |   20110070701 A   | 6/2011 |
| KR |   20110112606 A   | 10/2011 |
| KR |   20130007767 A   | 1/2013 |
| KR |   20130061777 A   | 6/2013 |

* cited by examiner

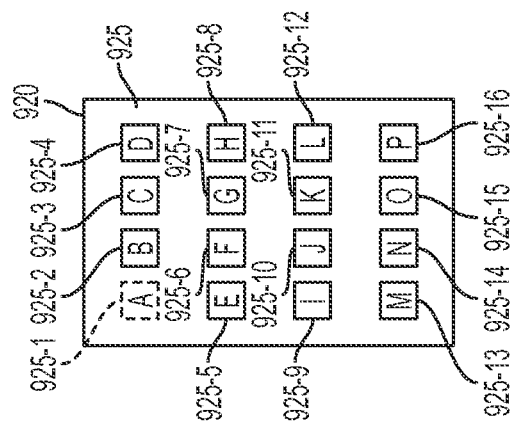
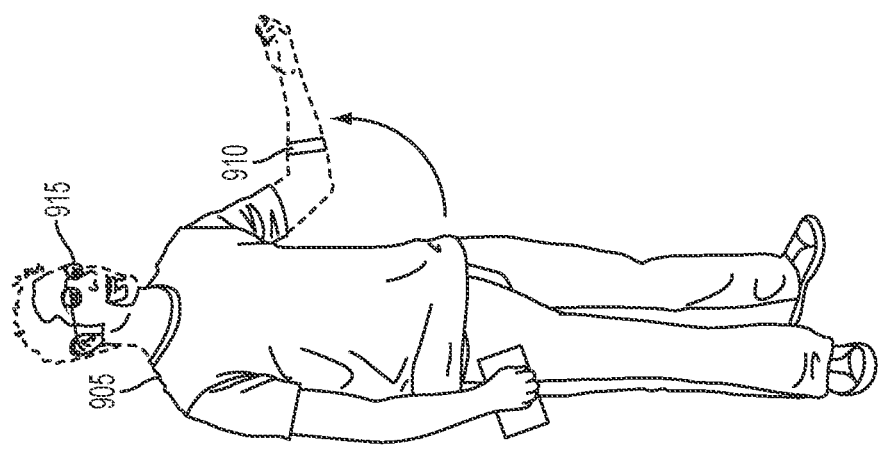
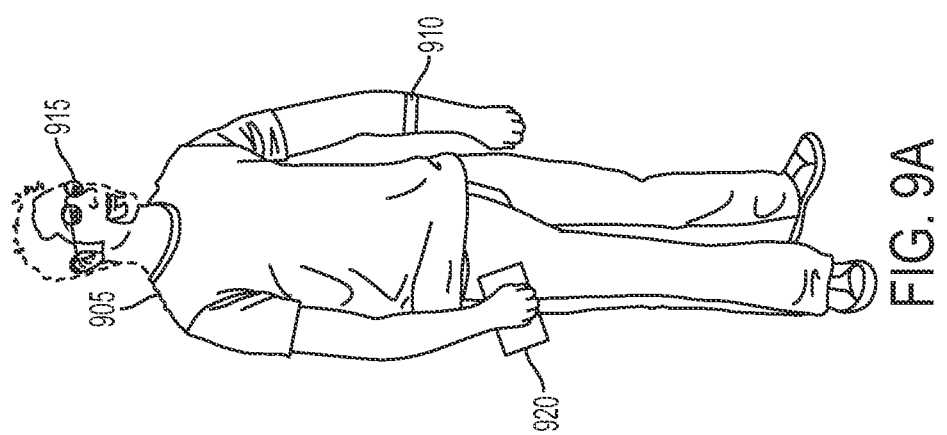

APPARATUS, SYSTEM, AND METHOD FOR TRANSFERRING DATA FROM A TERMINAL TO AN ELECTROMYOGRAPHY (EMG) DEVICE

TECHNICAL FIELD

The present disclosure relates to an apparatus, a system, and a method for communicating data between an Electromyography (EMG) device and at least one terminal. More particularly, the present disclosure relates to an apparatus and method for transmitting data from a terminal to the EMG device according to an event detected by the EMG device.

BACKGROUND

Mobile terminals are developed to provide wireless communication between users. As technology has advanced, mobile terminals now provide many additional features beyond simple telephone conversation. For example, mobile terminals are now able to provide additional functions such as an alarm, a Short Messaging Service (SMS), a Multimedia Message Service (MMS), E-mail, games, remote control of short range communication, an image capturing function using a mounted digital camera, a multimedia function for providing audio and video content, a scheduling function, and many more. With the plurality of features now provided, a mobile terminal has effectively become a necessity of daily life.

According to the related art, two devices may be paired using Near Field Communication (NFC). The paired devices may transfer data therebetween. However, the pairing of such devices requires that the two devices be smartphones. Such a method of transferring data between two paired devices is inconvenient, slow, unnatural, and lacks control.

Electromyography (EMG) is a technique for detecting, recording, and analyzing electrical signals generated by a muscle. Generally, muscle cells generate an electric potential when the muscle cells are electrically or neurologically activated. An electromyography is performed using an electromyograph (e.g., an EMG device).

According to the related art, an EMG device may communicate with a terminal so as to transmit data associated with the varying electric potential generated based on a user's movement.

Accordingly, there is a need for an apparatus and method for providing an improved user interface while reducing power consumption in a mobile terminal

SUMMARY

Aspects of the present disclosure are to address at least the above-mentioned problems and/or disadvantages and to provide at least the advantages described below. Accordingly, an aspect of the present disclosure is to provide an apparatus, a system, and a method for transferring data from a terminal to an electromyography (EMG) device.

In accordance with an aspect of the present disclosure, a method for transferring data from a source terminal to an EMG device is provided. The method includes detecting a user motion, determining whether the user motion corresponds to a motion associated with requesting data to be transferred from the source terminal to the EMG device, and if the user motion corresponds to a motion associated with requesting data to be transferred to from the source terminal to the EMG device, transmitting to the source terminal a request for the data according to the user motion.

In accordance with another aspect of the present disclosure, an EMG device is provided. The EMG device includes a sensor unit configured to detect user motion, a communication unit configured to transmit and receive data, and a control unit configured to determine whether the user motion corresponds to a motion associated with requesting data to be transferred from a source terminal to the EMG device, and to operatively transmit a request for the data to the source terminal according to the user motion.

In accordance with another aspect of the present disclosure, a source terminal is provided. The source includes a storage unit configured to store data, a communication unit configured to communicate with an EMG device, and a control unit to receive a request to transfer data to the EMG device according to a user motion detected by the EMG device, and to operatively transmit to the EMG device the data associated with the request.

In accordance with another aspect of the present disclosure, a target terminal is provided. The target terminal includes a storage unit configured to store data, a communication unit configured to communicate with an EMG device, a control unit to receive data from the EMG device according to a user motion detected by the EMG device, and to operatively store the data.

In accordance with another aspect of the present disclosure, a system for transferring data from a source terminal to an EMG device is provided. The system includes the EMG device, and the source terminal The EMG device may include a sensor unit configured to detect user motion, a communication unit configured to transmit and receive data, a control unit configured to determine whether the user motion corresponds to a motion associated with requesting data to be transferred from the source terminal to the EMG device, and to operatively transmit a request for the data to the source terminal according to the user motion. The source terminal may include a storage unit configured to store data, a communication unit configured to communicate with an EMG device, and a control unit to receive a request to transfer data to the EMG device according to a user motion detected by the EMG device, and to operatively transmit to the EMG device the data associated with the request.

In accordance with another aspect of the present disclosure, a method for pairing an EMG device with a terminal is provided. The method includes transmitting, by the EMG device, a signal, receiving, by the terminal, the signal transmitted by the EMG device, detecting, by the terminal, an input event, and establishing, by the terminal, a connection with the EMG device if the input event corresponds to a hovering event while the terminal is receiving the signal transmitted by the EMG device.

In accordance with another aspect of the present disclosure, a Head Mounted Display (HMD) device for displaying an augmented reality effect associated with an EMG device is provided. The HMD includes a display unit configured to display the augmented reality effect, and a control unit configured to display the augmented reality effect in relation to the EMG device according to a user motion detected by the EMG device.

Other aspects, advantages, and salient features of the disclosure will become apparent to those skilled in the art from the following detailed description, which, taken in conjunction with the annexed drawings, discloses various embodiments of the disclosure.

BRIEF DESCRIPTION OF THE DRAWINGS

The above and other aspects, features, and advantages of various embodiments of the present disclosure will be more apparent from the following description taken in conjunction with the accompanying drawings, in which:

FIGS. 9A, 9B, 9C, 9D, and 9E are illustrations of an EMG device used in conjunction with an electronic device according to various embodiments of the present disclosure.

Throughout the drawings, it should be noted that like reference numbers are used to depict the same or similar elements, features, and structures.

DETAILED DESCRIPTION

Figure 1:
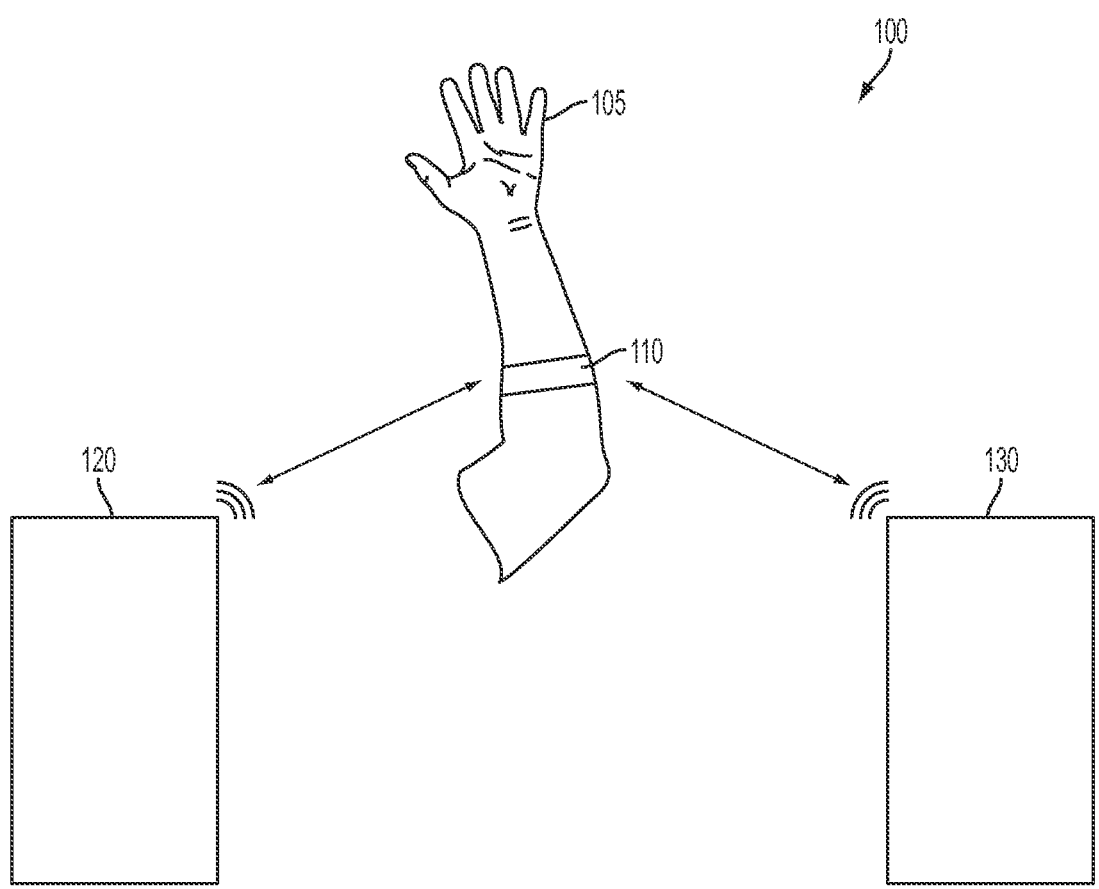
FIG. 1 is a diagram illustrating a system for transmitting data to an Electromyography (EMG) device according to an embodiment of the present disclosure.

The following description with reference to the accompanying drawings is provided to assist in a comprehensive understanding of various embodiments of the disclosure as defined by the claims and their equivalents. It includes various specific details to assist in that understanding, but these are to be regarded as merely exemplary. Accordingly, those of ordinary skill in the art will recognize that various changes and modifications of the embodiments described herein can be made without departing from the scope and spirit of the disclosure. In addition, descriptions of well-known functions and constructions are omitted for clarity and conciseness.

The terms and words used in the following description and claims are not limited to the bibliographical meanings, but, are merely used by the inventor to enable a clear and consistent understanding of the disclosure. Accordingly, it should be apparent to those skilled in the art that the following description of various embodiments of the present disclosure are provided for illustration purpose only and not for the purpose of limiting the disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

By the term "substantially" it is meant that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

As a non-exhaustive illustration only, a terminal described herein may refer to mobile devices such as a cellular phone, a Personal Digital Assistant (PDA), a digital camera, a portable game console, an MP3 player, a Portable/Personal Multimedia Player (PMP), a handheld e-book, a tablet PC, a portable lap-top PC, a Global Positioning System (GPS) navigation, and devices such as a desktop PC, a high definition television (HDTV), an optical disc player, a set-top box, and the like capable of wireless communication or network communication consistent with that disclosed herein.

According to the related art, an EMG device is an armband and may detect a motion of a user's arm and/or finger. The EMG device may transmit information to a terminal corresponding to the detected motion.

Various embodiments of the present disclosure include an apparatus, a system, and a method for transferring data from a terminal (e.g., a source terminal) to an EMG device.

According to various embodiments of the present disclosure, the EMG device may be an armband, a watch, and the like. According to various embodiments of the present disclosure, the EMG device is configured to measure muscle activity. The EMG device may measure the muscle activity of a user using EMG muscle sensors, dry electrodes, and/or the like.

According to various embodiments of the present disclosure, an EMG device may detect a motion and transmit data to the source terminal. In response to receipt of the data from the EMG device, the source terminal transfers data to the EMG device.

According to various embodiments of the present disclosure, the data transferred from the source terminal to the EMG device may be data identified (e.g., selected) by data transmitted from the EMG device to the source terminal (e.g., data requested by the EMG device). For example, the data to be transferred from the source terminal to the EMG device may be determined according to the type (or specific) motion detected by the EMG device. According to various embodiments of the present disclosure, the EMG device may transmit data corresponding to the electrical signals (e.g., waveform) detected by the EMG device based on the motion.

According to various embodiments of the present disclosure, the EMG device may analyze the electrical signals detected based on the motion of the user (e.g., the user's arm, fingers, and/or the like), and generate a request for data to be transferred from the source terminal. For example, the EMG device may store a mapping (or other identified associations) of motions to requests, commands, or the like. According to various embodiments of the present disclosure, upon detection of a motion of the user, the EMG device may determine whether the detected motion corresponds to a preconfigured request, command, and/or the like (e.g., based on the stored mapping), and if the detected motion corresponds to a preconfigured request, command, and/or the like, the EMG device may transmit such a request, command, and/or the like to the source terminal According to various embodiments of the present disclosure, the request, the command, and/or the like may correspond to a request to transfer to the EMG device the last media content reproduced (e.g., played, viewed, and/or the like) by the source terminal, a request to transfer to the EMG device the most recently received email, text message, or the like by the source terminal, a request to transfer to the EMG device the most recently viewed email, text message, or the like by the source terminal, and/or the like.

According to various embodiments of the present disclosure, the source terminal may analyze the electrical signals detected by the EMG device based on the motion of the user (e.g., the user's arm, fingers, and/or the like), and transmit corresponding data to the EMG device. For example, the source terminal may store a mapping (or other identified associations) of motions detected by the EMG device to particular functions. The source terminal may store a mapping of motions detected by the EMG device to functions for transmitting particular data to the EMG device. According to various embodiments of the present disclosure, upon receipt of data (e.g., corresponding to the motion detected by the EMG device), the source terminal may determine whether the detected motion corresponds to a preconfigured request, command, and/or the like (e.g., based on the stored mapping), and if the detected motion corresponds to a preconfigured request, command, and/or the like, the source terminal may perform a function corresponding to such a request, command, and/or the like. According to various embodiments of the present disclosure, the request, the command, and/or the like may correspond to a function of transferring to the EMG device the last media content reproduced (e.g., played, viewed, and/or the like) by the source terminal, a function of transferring to the EMG device the most recently received email, text message, or the like by the source terminal, a function of transferring to the EMG device the most recently viewed email, text message, or the like by the source terminal, and/or the like.

According to various embodiments of the present disclosure, the data transferred from the source terminal to the EMG device may be data identified (e.g., selected) by a user of the source terminal according to an input operatively input to the source terminal. For example, a user may contemporaneously input a selection to the source terminal (e.g. via a touchscreen input, a key, an audio input, and/or the like).

According to various embodiments of the present disclosure, the EMG device may use or otherwise process the data received from the source terminal For example, if the source terminal transfers an audio file to the EMG device, then the EMG device may playback the audio file according to user input thereto (e.g., the input may be a preconfigured motion). As another example, the EMG device may delete therefrom the data received from the source terminal according to user input thereto (e.g., the input may be a preconfigured motion). As another example, the EMG device may broadcast the data received from the source terminal according to user input thereto (e.g., the input may be a preconfigured motion). As another example, the EMG device may specifically transmit the data received from the source terminal to a target device according to user input thereto (e.g., the input may be a preconfigured motion such as a flick over the target device).

According to various embodiments of the present disclosure, the EMG device may transfer data to a target terminal For example, the EMG device may be used to retrieve data from a source terminal according to a detected motion, and the EMG device may thereafter transmit the data to a target terminal according to another detected motion. The EMG device may transfer data stored thereon to a target terminal Accordingly, the EMG device may facilitate transfer of data (e.g., media content, emails, documents, and the like) from a source terminal to a target terminal, whereby the EMG device serves as an intermediary. For example, the EMG device manages or otherwise facilitates the process of transferring data from the source terminal to the target terminal according to detected motions.

According to various embodiments of the present disclosure, the EMG device may communicate with a terminal (e.g., a source terminal, a target terminal, and/or the like) using wireless communication. For example, the EMG device may communicate using a wireless communication technology such as Bluetooth, or WiFi Direct. The EMG device may also communicating using other wireless communication technologies such as Infrared Data Association (IrDA) technology, WiFi, Near Field Communication (NFC), and/or the like.

According to various embodiments of the present disclosure, the EMG device may establish a connection with a terminal (e.g., a source terminal, a target terminal, and/or the like) based on a measured signal strength of the EMG device (e.g., the received signal strength being transmitted or broadcast from the EMG device). For example, the terminal may detect an EMG device based on a received signal. The terminal may measure the received signal and if the signal strength of the received signal is greater than or equal to a threshold value, then the terminal may establish connection with the EMG device. As an example, if the received signal is greater than or equal to the threshold value, then the terminal may pair with the EMG device.

According to various embodiments of the present disclosure, the EMG device may establish a connection with a terminal (e.g., a source terminal, a target terminal, and/or the like) based on a measured signal strength of the EMG device and a presence of an input event to the terminal For example, if the EMG device broadcasts data (e.g., a message such as an advertising message, content, and/or the like) in the vicinity of a plurality of terminals, there may be benefits associated with a terminal determining whether the data broadcast by the terminal is intended for that terminal. In addition, according to such an example, if the EMG device broadcasts the data in close proximity to a plurality of terminals, then the received signal strength at each of the terminals may exceed a threshold value used to determine whether to establish connection with the EMG device. Accordingly, there may be a need for another factor used to determine whether communication with a specific terminal is intended. According to various embodiments of the present disclosure, a terminal may determine to establish connection with the EMG device according to whether a received signal strength of a signal received from the EMG device is greater than or equal to a threshold, in conjunction with detection of an input event. According to various embodiments of the present disclosure, the input event may correspond to a hovering event. For example, the terminal may determine that a user's hand, fingers, input device (e.g., a stylus), and/or the like is hovering above the terminal. For example, the terminal may determine whether the user's hand, fingers, input device, and/or the like is hovering above a touchscreen of the terminal. As an example, detection of a hovering event may be indicative of the user intending to establish communication between the EMG device and the terminal detecting the hovering event (as opposed to other terminals that receive signals from the EMG device but do detect a hovering event) because of the inherent proximity of the EMG device to the terminal.

According to various embodiments of the present disclosure, a terminal may determine whether to establish a connection (e.g., pair with) an EMG device based on whether the terminal receives a signal from the EMG device and whether the terminal concurrently or contemporaneously detects a hovering event.

According to various embodiments of the present disclosure, a terminal may determine whether to establish a connection (e.g., pair with) an EMG device based on whether the terminal receives a signal from the EMG device and whether the terminal concurrently or contemporaneously detects a hovering event, while not detecting a touch event (or other express input to the terminal). According to various embodiments of the present disclosure, the terminal may determine to establish a connection with the EMG device if a signal strength of the signal received from the EMG device is also greater than or equal to a threshold.

According to various embodiments of the present disclosure, the motion detected by the EMG device may be a grasp gesture (e.g., moving the user's fingers from extended position to a clenched position), a drop gesture (e.g., moving the user's fingers from a clenched position to an extended position), a flick gesture (e.g., a flicking of a user's finger), a pull gesture (e.g., a grasp gesture in conjunction with a movement of the arm. According to various embodiments of the present disclosure, the EMG device may detect motions respectively corresponding to a flick of any specific finger. According to various embodiments of the present disclosure, the pull gesture may correspond to a movement of the user's arm away from a specific terminal, a grasp gesture in conjunction with movement of the user's arm, and/or the like.

According to various embodiments of the present disclosure, a terminal may display a User Interface (UI) event or element corresponding to the received instruction, request, or the like received from the EMG device. For example, the source terminal may display the removal or movement of an item on the UI when the EMG requests that the source terminal transfer the data (e.g., data corresponding to the item) to the EMG device. As another example, the source terminal may display an item on the UI being pulled away from a remaining portion of the UI when the EMG requests that the source terminal transfer the data to the EMG device.

According to various embodiments of the present disclosure, a terminal with which the EMG device (e.g., an armband) communicates may be a Head-Mounted Display (HMD) terminal The EMG device may transmit (e.g., stream) data corresponding to or otherwise associated with content stored in the EMG device. The HMD terminal may scan (on a periodic or a continual basis) for a unique identifier on the EMG device using a camera operatively connected to the HMD terminal. According to various embodiments of the present disclosure, if the HMD terminal detects the unique identifier on the EMG device, then the HMD terminal may display data present in the EMG device (e.g., the data being transmitted by the EMG device) over the user's field of view (e.g., so as to create an augmented reality of the EMG device with the data transmitted therefrom being displayed in association with the EMG device. As an example, if the EMG device is reproducing data (e.g., playing back a music file, a video file, and/or the like), then the HMD terminal may display an augmented reality in which an associated file (e.g., a music video) is displayed above or otherwise in association with the EMG device. As another example, if the EMG device stores user data to be copied and/or pasted, then the HMD terminal may display an augmented reality in which text associated with the user data is displayed above or otherwise in association with the EMG device. According to various embodiments of the present disclosure, the EMG device may require that the HMD terminal be authenticated before permitting or otherwise enabling the HMD terminal to display data associated with the EMG device. For example, the HMD terminal may be authenticated by a user pressing a button on the EMG device, performing a preconfigured motion, or the like, when the EMG device is in close proximity to the HMD terminal.

FIG. 1 is a diagram illustrating a system for transmitting data to an EMG device according to an embodiment of the present disclosure.

Referring to FIG. 1, a system 100 for transmitting data to an EMG device may include an EMG device 110 and a source terminal 120. The EMG device may be worn by a user 105.

According to various embodiments of the present disclosure, the EMG device 110 may detect a motion of the user 105. When the EMG device 110 detects a motion of the user 105, the EMG device may transmit an instruction, a request, data, and/or the like corresponding to the detected motion.

According to various embodiments of the present disclosure, the EMG device 110 may determine whether the motion corresponds to a preconfigured motion mapped to an instruction, a request, data, and/or the like, and thereafter perform a function corresponding to the instruction, the request, the data, and/or the like. For example, the EMG 110 may determine that the motion corresponds to a request to transfer data from the source terminal 120 to the EMG device 110. As a result, the EMG device 110 may communicate with the source terminal 120 and request transfer of the data from the source terminal 120. The source terminal 120 may thereafter communicate with the EMG device 110 to transfer the requested data.

As another example, the EMG device 110 may determine that the detected motion corresponds to a request to process or otherwise use data stored on the EMG device. For example, the EMG device 110 may determine that the detected motion corresponds to a user 105 request to playback content (e.g., an audio file, a video file, an image, and/or the like) stored on the EMG device 110. In response, the EMG device 110 may perform such a function (e.g., playback the content). As another example, the EMG device 110 may determine that the detected motion corresponds to a user 105 requesting that the EMG device 100 display data stored thereon. For example, if the EMG device 110received a communication (e.g., an email, a text message, and/or the like) or other document from a source terminal 120, and if the EMG device 110 determines that a user 104 motion corresponds to a request that the EMG device 110 display the communication or other document, then the EMG device 110may display the communication or other document (e.g., on a screen included on the EMG device 110). As another example, the EMG device 110 may determine that a user 105 motion corresponds to selection of a content stored on the EMG device 110. For example, if the EMG device 110 is playing back content stored thereon, and if the EMG device 110 detects a motion, the EMG device may determine that the motion corresponds to a request to advance to a next or previous content file (e.g., play the next song, play the previous song, and/or the like).

According to various embodiments of the present disclosure, the system 100 may also include a target terminal 130. The target terminal 130 may correspond to a terminal to which data is transferred from the EMG device 110. For example, data may be transferred from the EMG device 110 to the target terminal 130 according to a detected motion of the user 105.

According to various embodiments of the present disclosure, the EMG device 110 may establish a connection (e.g., pair with) one other terminal. According to various embodiments of the present disclosure, the EMG device 110 may establish a connection (e.g., pair with) a plurality of other terminal (e.g., a source terminal 120, a target terminal 130, and/or the like). According to various embodiments of the present disclosure, the EMG device 110 may establish a connection with a plurality of other terminals so as to communicate with the other terminals on a concurrent and/or contemporaneous basis.

According to various embodiments of the present disclosure, the terminal (e.g., the source terminal 120, the target terminal 130, and/or the like) may determine the request, instruction, and/or the like that corresponds to the detected motion. For example, the EMG device 110 may transmit to the terminal a waveform and/or the like corresponding to the detected motion. The terminal may thereafter analyze the received waveform and/or the like and determine whether a preconfigured request, instruction, and/or the like is stored in association with the detected motion.

According to various embodiments of the present disclosure, at least one of the EMG device 110, the source terminal 120, and the target terminal 130 may be configurable to by the user 105. For example, the user 105 may store (e.g., define) user and/or device settings according to which a motion is mapped to a function. According to various embodiments of the present disclosure, the at least one of the EMG device 110, the source terminal 120, and the target terminal 130 may operate a machine-learning algorithm by which the at least one of the EMG device 110, the source terminal 120, and the target terminal 130 learns (e.g., defines, stores, and/or the like) a user 105 motion. As an example, the machine-learning algorithm may be operated by the at least one of the EMG device 110, the source terminal 120, and the target terminal 130 in order to configure new user 105 motions in association with at least one function, to calibrate the EMG device 110, and/or the like.

Figure 2:
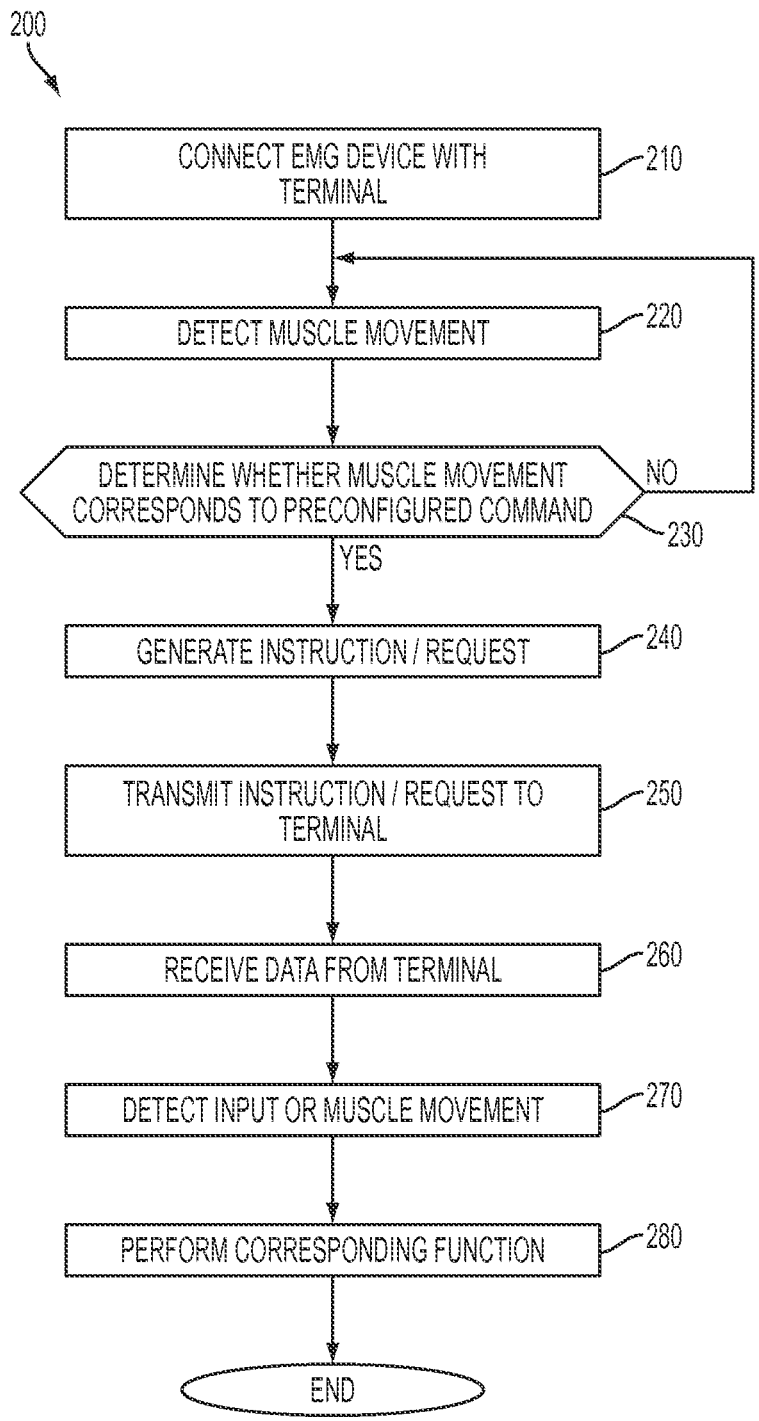
FIG. 2 is a flowchart illustrating a method of transmitting data to an EMG device according to an embodiment of the present disclosure.

FIG. 2 is a flowchart illustrating a method of transmitting data to an EMG device according to an embodiment of the present disclosure;

Referring to FIG. 2, at operation 210 a terminal (e.g., the source terminal, the target terminal, and/or the like) is connected with an EMG device. According to various embodiments of the present disclosure, the EMG device may be connected with a plurality of terminals on a concurrent and/or contemporaneous basis. For example, the EMG device may be paired with the source terminal and the target terminal simultaneously using a wireless communication technology such as WiFi Direct, and/or the like.

At operation 220, the EMG device detects a movement. For example, the EMG device detects a user's muscle movement. According to various embodiments of the present disclosure, the EMG device may recognize the movement based on analysis of various information detected by sensors included in the EMG device. According to various embodiments of the present disclosure, the EMG device may stream data associated with the various information detected by sensors included in the EMG device with which terminals connected to the EMG device may detect the movement based on analysis of the information received by the EMG device.

At operation 230, the detected movement is analyzed to determine whether the movement (e.g., user movement, muscle movement, or the like) corresponds to a preconfigured command (e.g., a request, instruction, and/or the like). According to various embodiments of the present disclosure, the EMG device may compare the various information detected by sensors included in the EMG device with information stored on the EMG device, and if the information detected by the sensors matches the information stored on the EMG device (e.g., within a predefined standard of deviation, and/or confidence interval), then the EMG device may determine that the user movement corresponds to a preconfigured command. For example, the EMG device may determine whether the detected user movement corresponds to a request for the terminal (e.g., the source terminal) to transfer data to the EMG device.

If the detected movement is determined to not correspond to a preconfigured command at operation 230, then the method may return to operation 220 at which movement is detected. For example, if the EMG device determines that the detected movement does not correspond to a preconfigured command stored in association with a mapping to a movement, then the EMG device may return to operation 220.

In contrast, if the detected movement is determined to correspond to a preconfigured command at operation 230, then the method may proceed to operation 240. For example, if the EMG device determines that the detected movement corresponds to a user movement stored in association with a mapping to a movement, then the EMG device may proceed to operation 240 at which an instruction, request, or the like is generated.

At operation 240, the EMG device may generate an instruction, request, or the like corresponding to the preconfigured command associated with the detected movement. For example, if the preconfigured command corresponds to a request for the transfer source terminal to transfer data to the EMG device, then the EMG device generates a request requesting the source terminal to transfer data to the EMG device. The EMG device may generate a request specifically identifying the data for which the request for the source terminal to transfer data relates.

At operation 250, the EMG device transmits the generated instruction, request, or the like to the source terminal.

At operation 260, the EMG device receives data from the source terminal. For example, in response to receiving the generated instruction, request, or the like from the EMG device, the source terminal may transfer the corresponding requested data to the EMG device.

At operation 270, the EMG device detects a movement. For example, the EMG device detects a user's muscle movement. According to various embodiments of the present disclosure, the EMG device may recognize the movement based on analysis of various information detected by sensors included in the EMG device. According to various embodiments of the present disclosure, the EMG device may stream data associated with the various information detected by sensors included in the EMG device with which terminals connected to the EMG device may detect the movement based on analysis of the information received by the EMG device.

At operation 280, the EMG device performs a function corresponding to the detected movement. For example, if the function corresponding to the detected motion corresponds to a request to playback data stored on the EMG device, then the EMG device may playback the data. As another example, if the function corresponding to the detected movement corresponds to navigation of data stored on the EMG device (e.g., navigation through media content being played by the EMG device, or the like), then the EMG device may navigate the data accordingly.

Figure 3:
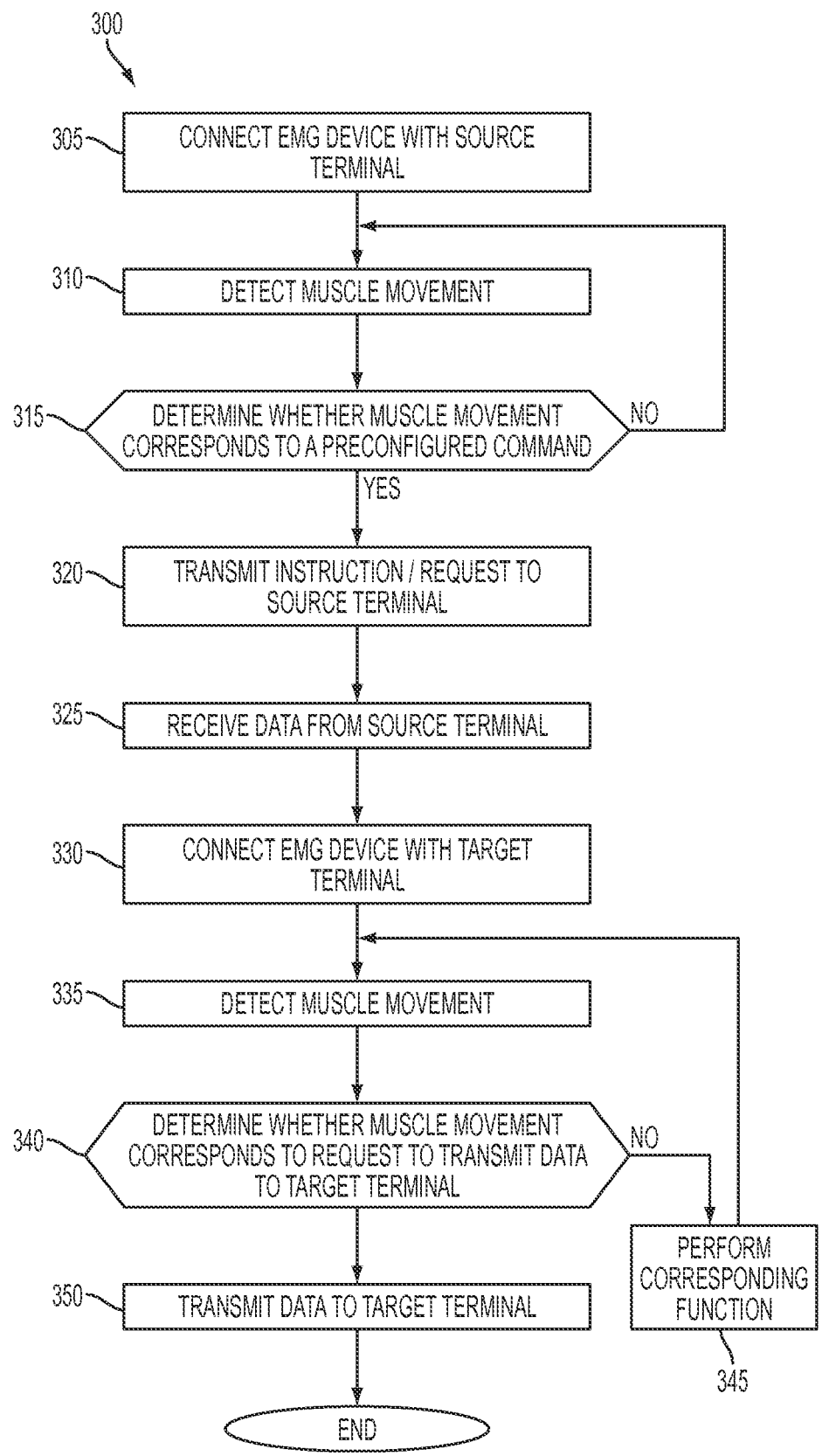
FIG. 3 is a flowchart illustrating a method of transmitting data from a target device to a source device using EMG device according to an embodiment of the present disclosure.

FIG. 3 is a flowchart illustrating a method of transmitting data from a target device to a source device using EMG device according to an embodiment of the present disclosure.

Referring to FIG. 3, at operation 305, the EMG device is connected with the source terminal According to various embodiments of the present disclosure, the EMG device may be connected with a plurality of terminals on a concurrent and/or contemporaneous basis. For example, the EMG device may be paired with the source terminal and the target terminal simultaneously using a wireless communication technology such as WiFi Direct, and/or the like.

At operation 310, the EMG device detects a movement. For example, the EMG device detects a user's muscle movement. According to various embodiments of the present disclosure, the EMG device may recognize the movement based on analysis of various information detected by sensors included in the EMG device. According to various embodiments of the present disclosure, the EMG device may stream data associated with the various information detected by sensors included in the EMG device with which terminals connected to the EMG device may detect the movement based on analysis of the information received by the EMG device.

At operation 315, the detected movement is analyzed to determine whether the movement (e.g., user movement, muscle movement, or the like) corresponds to a preconfigured command (e.g., a request, instruction, and/or the like). According to various embodiments of the present disclosure, the EMG device may compare the various information detected by sensors included in the EMG device with information stored on the EMG device, and if the information detected by the sensors matches the information stored on the EMG device (e.g., within a predefined standard of deviation, and/or confidence interval), then the EMG device may determine that the user movement corresponds to a preconfigured command. For example, the EMG device may determine whether the detected user movement corresponds to a request for the terminal (e.g., the source terminal) to transfer data to the EMG device.

If the detected movement is determined to not correspond to a preconfigured command at operation 315, then the method may return to operation 310 at which movement is detected. For example, if the EMG device determines that the detected movement does not correspond to a preconfigured command stored in association with a mapping to a movement, then the EMG device may return to operation 310.

In contrast, if the detected movement is determined to correspond to a preconfigured command operation 315, then the method may proceed to operation 320. For example, if the EMG device determines that the detected movement corresponds to a user movement stored in association with a mapping to a movement, then the EMG device may proceed to operation 320 at which an instruction, request, or the like is transmitted to the source terminal.

At operation 325, the EMG device receives data from the source terminal. For example, in response to receiving the instruction, request, or the like from the EMG device, the source terminal may transfer the corresponding requested data to the EMG device.

At operation 330, the EMG device is connected with the target terminal According to various embodiments of the present disclosure, the EMG device may be connected with a plurality of terminals on a concurrent and/or contemporaneous basis. For example, the EMG device may be paired with the source terminal and the target terminal simultaneously using a wireless communication technology such as WiFi Direct, and/or the like. According to various embodiments of the present disclosure, operation 330 may be combined with operation 305 such that the EMG device contemporaneously connects with the source terminal and the target terminal. According to various embodiments of the present disclosure, the EMG device may connect with the target terminal before are contemporaneous with operations 305, 310, 320, and 325.

At operation 335, the EMG device detects a movement. For example, the EMG device detects a user's muscle movement. According to various embodiments of the present disclosure, the EMG device may recognize the movement based on analysis of various information detected by sensors included in the EMG device. According to various embodiments of the present disclosure, the EMG device may stream data associated with the various information detected by sensors included in the EMG device with which terminals connected to the EMG device may detect the movement based on analysis of the information received by the EMG device.

At operation 340, the detected movement is analyzed to determine whether the movement (e.g., user movement, muscle movement, or the like) corresponds to a command (e.g., a request, instruction, and/or the like) to transfer data to the target terminal According to various embodiments of the present disclosure, the EMG device may compare the various information detected by sensors included in the EMG device with information stored on the EMG device, and if the information detected by the sensors matches the information stored on the EMG device (e.g., within a predefined standard of deviation, and/or confidence interval), then the EMG device may determine that the user movement corresponds to a command to transfer data to the target terminal.

If the detected movement is determined not to correspond to a command to transfer data to the target terminal at operation 340, then the EMG device may proceed to operation 345 at which the EMG performs a corresponding function (e.g., if the detected movement has a function associated therewith). Thereafter, the EMG device may return to operation 335 at which the EMG detects a movement (e.g., a new or different movement).

In contrast, if the detected movement is determined to correspond to a command to transfer data to the target terminal at operation 340, then the EMG device may proceed to operation 350 at which the target terminal transmits the corresponding data to the target terminal.

Figure 4:
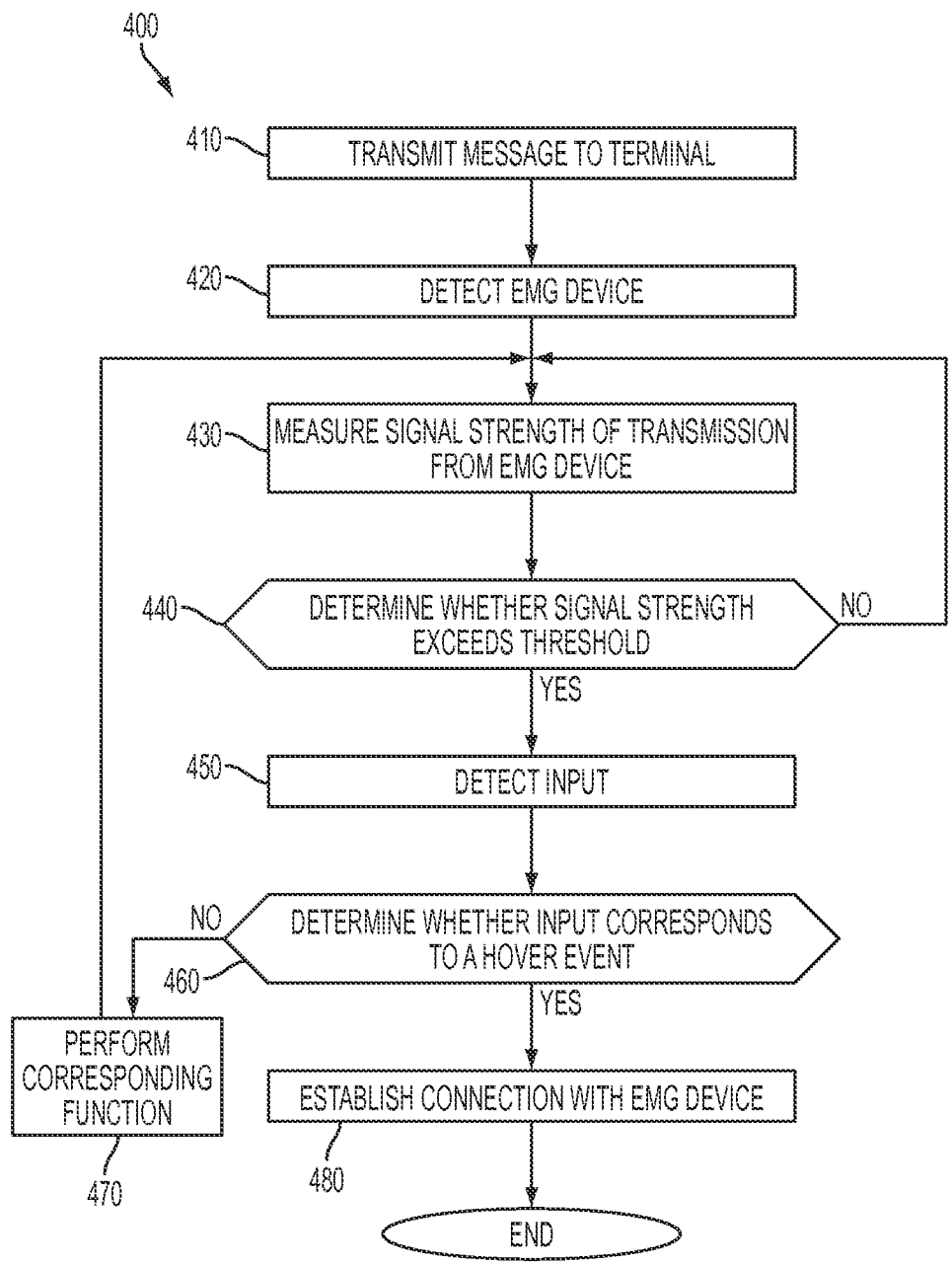
FIG. 4 is a flowchart illustrating a method of pairing an EMG device with a terminal according to an embodiment of the present disclosure.

FIG. 4 is a flowchart illustrating a method of pairing an EMG device with a terminal according to an embodiment of the present disclosure.

Referring to FIG. 4, at operation 410, the EMG device transmits a message to a terminal (e.g., a source terminal, a target terminal, and/or the like). According to various embodiments of the present disclosure, the EMG device may broadcast a message such as an advertisement message, and/or the like.

At operation 420, the terminal detects the EMG device. For example, the terminal receives the message transmitted by the EMG device.

At operation 430, the terminal measures the strength of the signal strength of the transmission from the EMG device.

At operation 440, the terminal determines whether the measured signal strength of the transmission from the EMG device exceeds a threshold. According to various embodiments of the present disclosure, the terminal may determine whether the measured signal of the transmission from the EMG device is greater than or equal to the threshold.

If the terminal determines that the measured signal strength of the transmission from the EMG device does not exceed the threshold at operation 440, then the terminal may return to operation 430.

In contrast, if the terminal determines that the measured signal strength of the transmission from the EMG device exceeds the threshold at operation 440, then the terminal may proceed to operation 450 at which the terminal detects an input.

At operation 460, the terminal determines whether the detected input corresponds to a hover event. As an example, the terminal may further determine whether the hover event is maintained for a threshold period of time.

If the terminal determines that the detected input does not correspond to a hover event at operation 460, then the terminal may proceed to operation 470 at which the terminal performs a corresponding function.

In contrast, if the terminal determines that the detected input corresponds to a hover event at operation 460, then the terminal may proceed to operation 480 at which the terminal establishes a connection with the EMG device. For example, the terminal may pair with the EMG device. According to various embodiments of the present disclosure, the terminal may establish a connection with the EMG device if the hover event is maintained for at least a threshold period of time in conjunction with the measured signal strength of the transmission from the EMG device.

Figure 5:
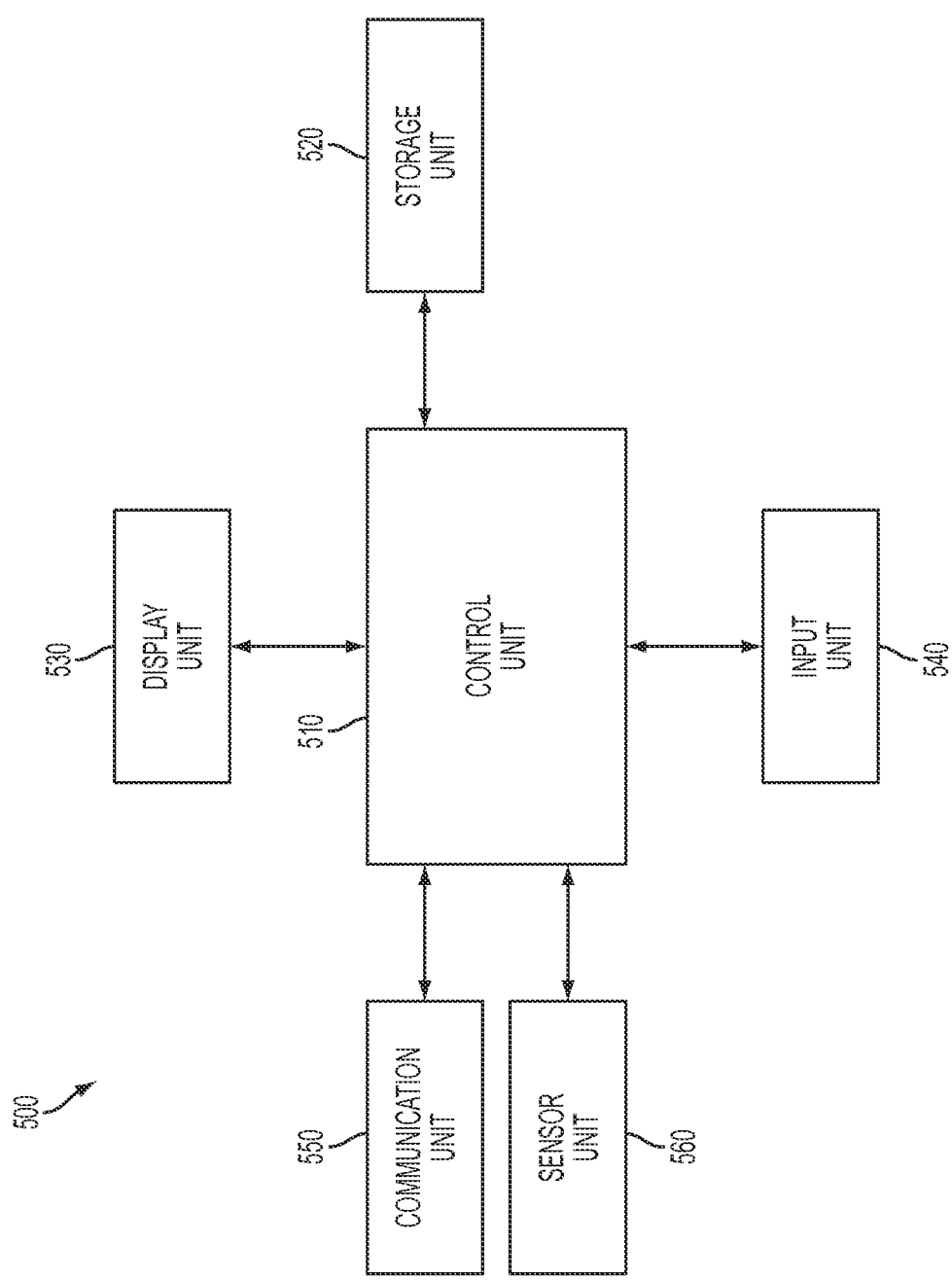
FIG. 5 is a block diagram of an EMG device according to an embodiment of the present disclosure.

FIG. 5 is a block diagram of an EMG device according to an embodiment of the present disclosure.

Referring to FIG. 5, the EMG device 500 may include a control unit 510, a storage unit 520, a communication unit 550, and a sensor unit 560. According to various embodiments of the present disclosure, the EMG device 500 may also include a display unit 530, an input unit 540, and/or the like.

According to various embodiments of the present disclosure, the EMG device 500 comprises at least one control unit 510. The at least one control unit 510 may be configured to operatively control the EMG device 500. For example, the at least one control unit 510 may control operation of the various components or units included in the EMG device 500. The at least one control unit 510 may transmit a signal to the various components included in the EMG device 500 and control a signal flow between internal blocks of the EMG device 500. In particular, according to various embodiments of the present disclosure, the at least one control unit 510 may perform an action (e.g., a command, function, or the like) according to an input. For example, the at least one control unit 510 may display items on a UI according to user input. The at least one control unit 510 may select items a UI according to user input. In addition, the at least one control unit 510 may perform a corresponding function associated with an application with which a user interacted (e.g., selected). The at least one control unit 510 may analyze information received by the sensor unit 560 corresponding to a motion (e.g., a user's motion, a muscle motion, and/or the like). The at least one control unit 510 may operatively request that a source terminal transfer data to the EMG device according to the motion. The at least one control unit 510 may operatively transfer data to a target terminal according to the motion. The at least one control unit 510 may reproduce (e.g., playback) or otherwise process data stored in the storage unit 520 according to the motion.

The storage unit 520 can store user data, and the like, as well a program which performs operating functions according to various embodiments of the present disclosure. The storage unit 520 may include a non-transitory computer-readable storage medium. As an example, the storage unit 520 may store a program for controlling general operation of the EMG device 500, an Operating System (OS) which boots the EMG device 500, and application program for performing other optional functions such as a camera function, a sound replay function, an image or video replay function, a signal strength measurement function, a route generation function, image processing, and the like. Further, the storage unit 520 may store user data generated according to a user of the EMG device 500, such as, for example, a text message, a game file, a music file, a movie file, and the like. In particular, according to various embodiments of the present disclosure, the storage unit 520 may store an application or a plurality of applications that individually or in combination analyze a motion detected by the sensor unit 560, operatively determine whether the motion corresponds to a preconfigured command, and perform a corresponding function associated the motion (e.g., selected). According to various embodiments of the present disclosure, the storage unit 520 may store a mapping of at least one motion to at least one command, function, or the like.

The communication unit 550 may be configured for communicating with other devices. For example, the communication unit 550 may be configured to communicate via Bluetooth technology, WiFi technology, WiFi Direct technology, IrDA technology, NFC technology, or another wireless technology.

According to various embodiments of the present disclosure, the EMG device 500 may include a display unit 530. The display unit 530 displays information inputted by user or information to be provided to user as well as various menus of the EMG device 500. For example, the display unit 530 may provide various screens of the EMG device 500, such as an idle screen, a message writing screen, a calling screen, and the like. In particular, according to various embodiments of the present disclosure, the display unit 530 may display an image and/or UI from which the user may interact with (e.g., select) a command and/or an item. According to various embodiments of the present disclosure, the display unit 530 may be a touchscreen. According to various embodiments of the present disclosure, the user may enter to the display unit 530 an input for requesting interaction with an item on the UI or an item stored on the EMG device 500 (e.g., playback of a media content), and/or the like. According to various embodiments of the present disclosure, the display unit 530 may display an interface which the user may manipulate or otherwise enter inputs via a touchscreen to enter selection of various functions of the EMG device 500. The display unit 530 can be formed as a Liquid Crystal Display (LCD), an Organic Light Emitting Diode (OLED), an Active Matrix Organic Light Emitting Diode (AMOLED), and the like. However, various embodiments of the present disclosure are not limited to these examples. Further, the display unit 530 can perform the function of the input unit 540.

According to various embodiments of the present disclosure, the EMG device 500 may include an input unit 540. The input unit 540 may include input keys and function keys for receiving user input. For example, the input unit 540 may include input keys and function keys for receiving an input of numbers or various sets of letter information, setting various functions, and controlling functions of the EMG device 500. For example, the input unit 540 may include a calling key for requesting a voice call, a video call request key for requesting a video call, a termination key for requesting termination of a voice call or a video call, a volume key for adjusting output volume of an audio signal, a direction key, and the like. In particular, according to various embodiments of the present disclosure, the input unit 540 may transmit to the at least one control unit 510 signals related to playing back media content stored on the EMG device 500. The input unit 540 may be formed by one or a combination of input means such as a touch pad, a touchscreen, a button-type key pad, a joystick, a wheel key, and the like.

Figure 6:
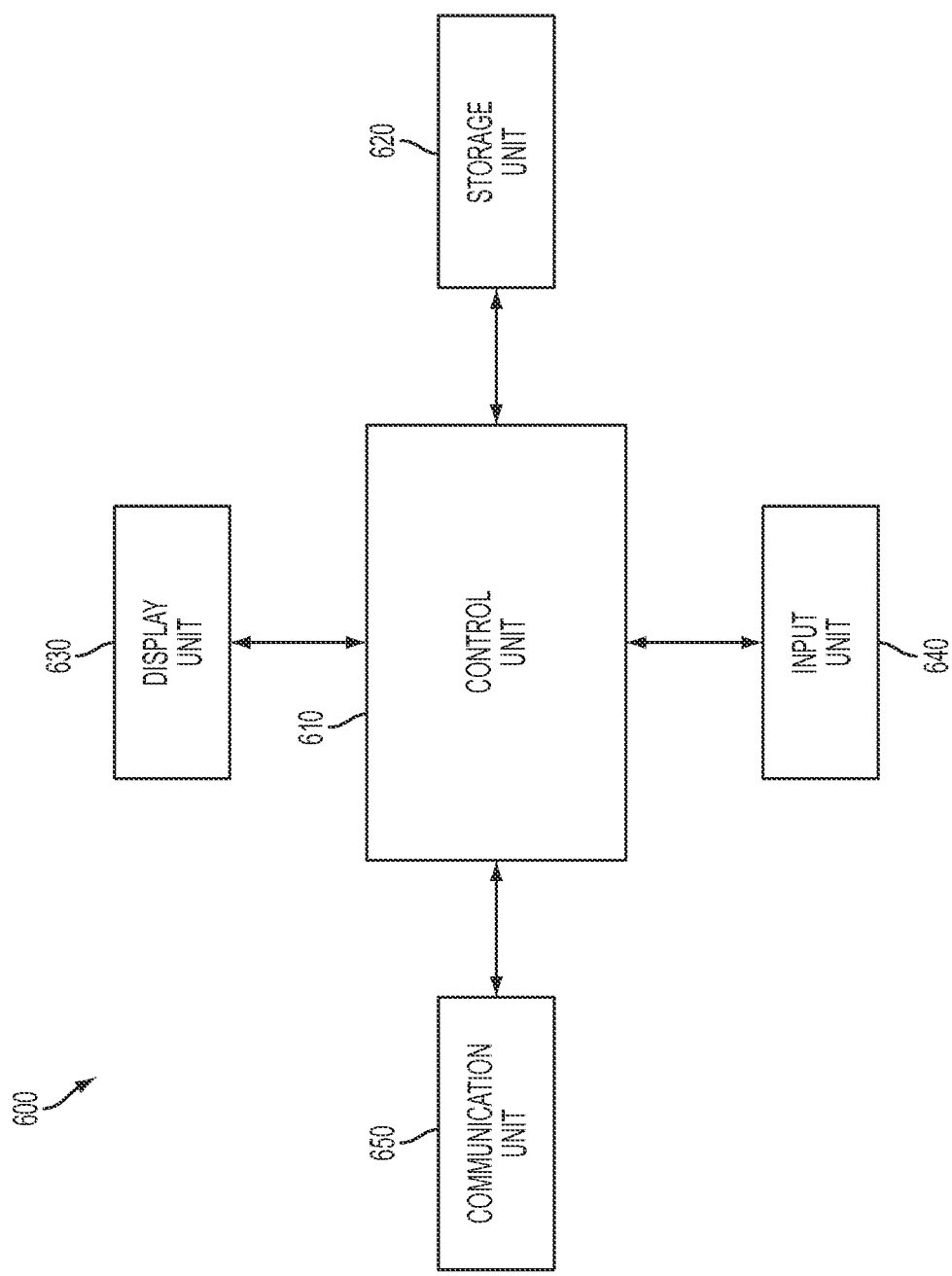
FIG. 6 is a block diagram of a source terminal according to various embodiments of the present disclosure.

FIG. 6 is a block diagram of a source terminal according to various embodiments of the present disclosure.

Referring to FIG. 6, the source terminal 600 may include a control unit 610, a storage unit 620, and a communication unit 650. According to various embodiments of the present disclosure, the source terminal 600 may also include a display unit 630, an input unit 640, and/or the like.

According to various embodiments of the present disclosure, the source terminal 600 comprises at least one control unit 610. The at least one control unit 610 may be configured to operatively control the source terminal 600. For example, the at least one control unit 610 may control operation of the various components or units included in the source terminal 600. The at least one control unit 610 may transmit a signal to the various components included in the source terminal 600 and control a signal flow between internal blocks of the source terminal 600. In particular, according to various embodiments of the present disclosure, the at least one control unit 610 may perform an action (e.g., a command, function, or the like) according to an input, received data (e.g. a request transmitted by an EMG device), and/or the like. For example, the at least one control unit 610 may display items on a UI according to user input. The at least one control unit 610 may select items a UI according to user input. In addition, the at least one control unit 610 may perform a corresponding function associated with an application with which a user interacted (e.g., selected). The at least one control unit 610 may analyze information received by the EMG device corresponding to a motion (e.g., a user's motion, a muscle motion, and/or the like). The at least one control unit 610 may operatively transmit to the EMG device data requested according to the motion. The at least one control unit 610 may reproduce (e.g., playback) or otherwise process data stored in the storage unit 620 according to the motion.

The storage unit 620 can store user data, and the like, as well a program which performs operating functions according to various embodiments of the present disclosure. The storage unit 620 may include a non-transitory computer-readable storage medium. As an example, the storage unit 620 may store a program for controlling general operation of source terminal 600, an Operating System (OS) which boots source terminal 600, and application program for performing other optional functions such as a camera function, a sound replay function, an image or video replay function, a signal strength measurement function, a route generation function, image processing, and the like. Further, the storage unit 620 may store user data generated according to a user of source terminal 600, such as, for example, a text message, a game file, a music file, a movie file, and the like. In particular, according to various embodiments of the present disclosure, the storage unit 620 may store an application or a plurality of applications that individually or in combination analyze a motion detected by the EMG device, operatively determine whether the motion corresponds to a preconfigured command, and perform a corresponding function associated the motion (e.g., selected). According to various embodiments of the present disclosure, the storage unit 620 may store a mapping of at least one motion to at least one command, function, or the like.

The communication unit 650 may be configured for communicating with other devices. For example, the communication unit 650 may be configured to communicate via Bluetooth technology, WiFi technology, WiFi Direct technology, IrDA technology, NFC technology, or another wireless technology.

According to various embodiments of the present disclosure, the source terminal 600 may include a display unit 630. The display unit 630 displays information inputted by user or information to be provided to user as well as various menus of the source terminal 600. For example, the display unit 630 may provide various screens of the source terminal 600, such as an idle screen, a message writing screen, a calling screen, and the like. In particular, according to various embodiments of the present disclosure, the display unit 630 may display an image and/or UI from which the user may interact with (e.g., select) a command and/or an item. According to various embodiments of the present disclosure, the display unit 630 may be a touchscreen. According to various embodiments of the present disclosure, the user may enter to the display unit 630 an input for requesting interaction with an item on the UI or an item stored on the source terminal 600 (e.g., playback of a media content), and/or the like. According to various embodiments of the present disclosure, the display unit 630 may display an interface which the user may manipulate or otherwise enter inputs via a touchscreen to enter selection of various functions of the source terminal 600. The display unit 630 can be formed as a Liquid Crystal Display (LCD), an Organic Light Emitting Diode (OLED), an Active Matrix Organic Light Emitting Diode (AMOLED), and the like. However, various embodiments of the present disclosure are not limited to these examples. Further, the display unit 630 can perform the function of the input unit 640.

According to various embodiments of the present disclosure, the source terminal 600 may include an input unit 640. The input unit 640 may include input keys and function keys for receiving user input. For example, the input unit 640 may include input keys and function keys for receiving an input of numbers or various sets of letter information, setting various functions, and controlling functions of the source terminal 600. For example, the input unit 640 may include a calling key for requesting a voice call, a video call request key for requesting a video call, a termination key for requesting termination of a voice call or a video call, a volume key for adjusting output volume of an audio signal, a direction key, and the like. In particular, according to various embodiments of the present disclosure, the input unit may 640 transmit to the at least one control unit 610 signals related to transferring data to the EMG device and/or receiving data from the EMG device. For example, the input unit 640 may be configured to detect a hovering event. The input unit 640 may be formed by one or a combination of input means such as a touch pad, a touchscreen, a button-type key pad, a joystick, a wheel key, and the like.

Figure 7:
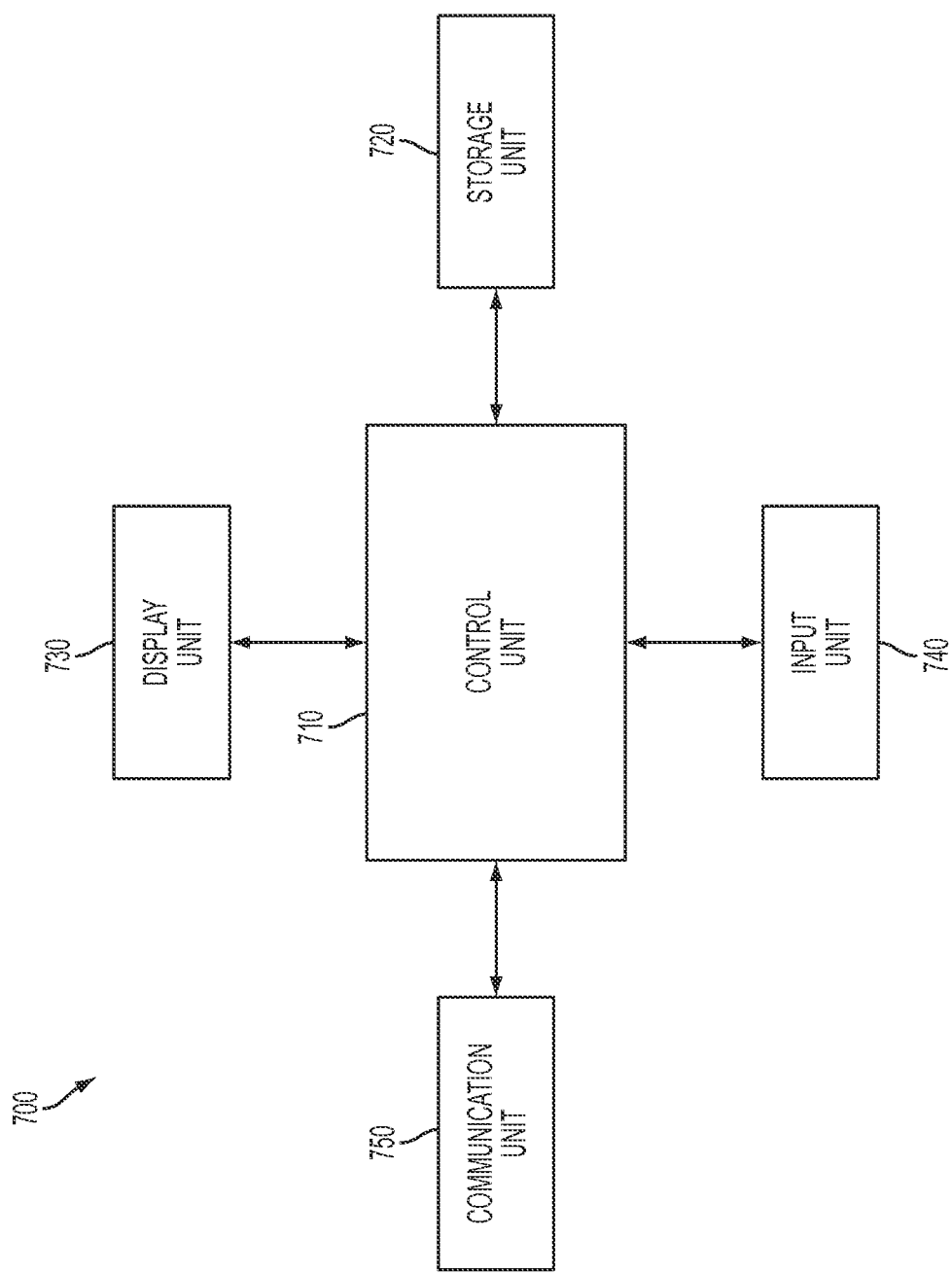
FIG. 7 is a block diagram of a target terminal according to various embodiments of the present disclosure.

FIG. 7 is a block diagram of a target terminal according to various embodiments of the present disclosure.

Referring to FIG. 7, the target terminal 70 may include a control unit 710, a storage unit 720, and a communication unit 750. According to various embodiments of the present disclosure, the target terminal 700 may also include a display unit 730, an input unit 740, and/or the like.

According to various embodiments of the present disclosure, the target terminal 700 comprises at least one control unit 710. The at least one control unit 710 may be configured to operatively control the target terminal 700. For example, the at least one control unit 710 may control operation of the various components or units included in the target terminal 700. The at least one control unit 710 may transmit a signal to the various components included in the target terminal 700 and control a signal flow between internal blocks of the target terminal 700. In particular, according to various embodiments of the present disclosure, the at least one control unit 710 may perform an action (e.g., a command, function, or the like) according to an input, received data (e.g. a data transmitted by an EMG device), and/or the like. For example, the at least one control unit 710 may display items on a UI according to user input. The at least one control unit 710 may select items a UI according to user input. In addition, the at least one control unit 710 may perform a corresponding function associated with an application with which a user interacted (e.g., selected). The at least one control unit 710 may analyze information received by the EMG device corresponding to a motion (e.g., a user's motion, a muscle motion, and/or the like). The at least one control unit 710 may operatively transmit to the EMG device data requested according to the motion, a request for data stored on the EMG device according to the motion, and/or the like. The at least one control unit 710 may reproduce (e.g., playback) or otherwise process data stored in the storage unit 720 according to the motion.

The storage unit 720 can store user data, and the like, as well a program which performs operating functions according to various embodiments of the present disclosure. The storage unit 720 may include a non-transitory computer-readable storage medium. As an example, the storage unit 720 may store a program for controlling general operation of target terminal 700, an Operating System (OS) which boots target terminal 700, and application program for performing other optional functions such as a camera function, a sound replay function, an image or video replay function, a signal strength measurement function, a route generation function, image processing, and the like. Further, the storage unit 720 may store user data generated according to a user of target terminal 700, such as, for example, a text message, a game file, a music file, a movie file, and the like. In particular, according to various embodiments of the present disclosure, the storage unit 720 may store an application or a plurality of applications that individually or in combination analyze a motion detected by the EMG device, operatively determine whether the motion corresponds to a preconfigured command, and perform a corresponding function associated the motion (e.g., selected). According to various embodiments of the present disclosure, the storage unit 720 may store a mapping of at least one motion to at least one command, function, or the like.

The communication unit 750 may be configured for communicating with other devices. For example, the communication unit 750 may be configured to communicate via Bluetooth technology, WiFi technology, WiFi Direct technology, IrDA technology, NFC technology, or another wireless technology.

According to various embodiments of the present disclosure, the target terminal 700 may include a display unit 730. The display unit 730 displays information inputted by user or information to be provided to user as well as various menus of the target terminal 700. For example, the display unit 730 may provide various screens of the target terminal 700, such as an idle screen, a message writing screen, a calling screen, and the like. In particular, according to various embodiments of the present disclosure, the display unit 730 may display an image and/or UI from which the user may interact with (e.g., select) a command and/or an item. According to various embodiments of the present disclosure, the display unit 730 may be a touchscreen. According to various embodiments of the present disclosure, the user may enter to the display unit 730 an input for requesting interaction with an item on the UI or an item stored on the target terminal 700 (e.g., playback of a media content), and/or the like. According to various embodiments of the present disclosure, the display unit 730 may display an interface which the user may manipulate or otherwise enter inputs via a touchscreen to enter selection of various functions of the target terminal 700. The display unit 730 can be formed as a Liquid Crystal Display (LCD), an Organic Light Emitting Diode (OLED), an Active Matrix Organic Light Emitting Diode (AMOLED), and the like. However, various embodiments of the present disclosure are not limited to these examples. Further, the display unit 730 can perform the function of the input unit 740.

According to various embodiments of the present disclosure, the target terminal 700 may include an input unit 740. The input unit 740 may include input keys and function keys for receiving user input. For example, the input unit 740 may include input keys and function keys for receiving an input of numbers or various sets of letter information, setting various functions, and controlling functions of the target terminal 700. For example, the input unit 740 may include a calling key for requesting a voice call, a video call request key for requesting a video call, a termination key for requesting termination of a voice call or a video call, a volume key for adjusting output volume of an audio signal, a direction key, and the like. In particular, according to various embodiments of the present disclosure, the input unit 740 may transmit to the at least one control unit 710 signals related to transferring data to the EMG device and/or receiving data from the EMG device. For example, the input unit 740 may be configured to detect a hovering event. The input unit 740 may be formed by one or a combination of input means such as a touch pad, a touchscreen, a button-type key pad, a joystick, a wheel key, and the like.

Figure 8B:
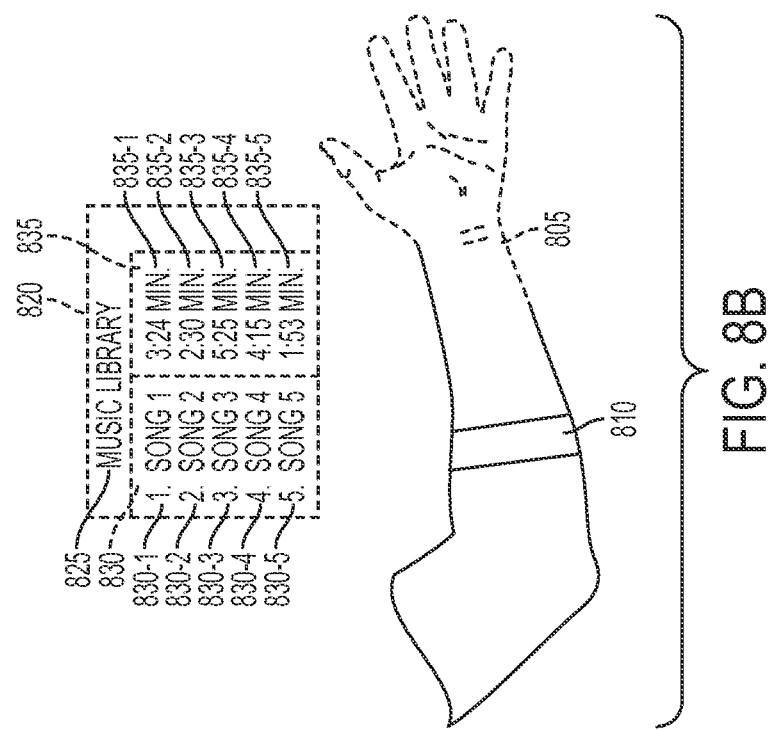
FIGS. 8A and 8B are illustrations of an EMG device used in conjunction with an electronic device according to various embodiments of the present disclosure.
Figure 8A:
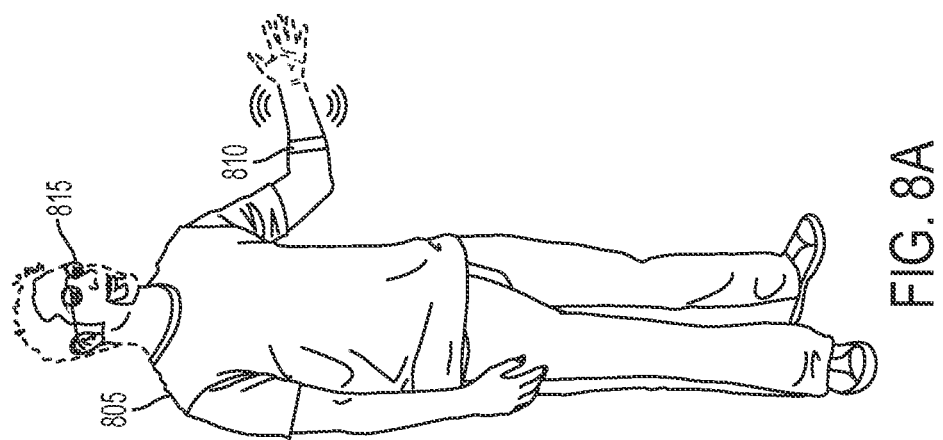

FIGS. 8A and 8B are illustrations of an EMG device used in conjunction with an electronic device according to various embodiments of the present disclosure.

Referring to FIG. 8A, a user 805 uses an EMG device 810 in conjunction with an electronic device. For example, according to various embodiments of the present disclosure, the user 805 may use the EMG device 810 in conjunction with HMD terminal 815.

According to various embodiments of the present disclosure, the EMG device 810 may be an armband, a wristwatch, and/or the like.

According to various embodiments of the present disclosure, the EMG device 810 may operatively communicate with the HMD terminal 815. For example, the EMG device 810 may be paired with the HMD terminal 815. As another example, the EMG device 810 may communicate with the HMD terminal 815 through another mobile terminal (e.g., a smartphone, and/or the like) to which both the EMG device 810 and the HMD terminal 815 are connected.

According to various embodiments of the present disclosure, the EMG device 810 may detect movement of the user 805. For example, as illustrated in FIG. 8A, the EMG device 810 may detect motion of the user's 805 arm.

According to various embodiments of the present disclosure, the EMG device 810 may communicate data to the HMD terminal 815. According to various embodiments of the present disclosure, the EMG device 810 may communicate to the HMD terminal 815 using a wireless communication technology such as Bluetooth, WiFi, WiFi Direct, NFC, IrDA, and/or the like.

According to various embodiments of the present disclosure, the EMG device 810 may communicate information associated with the detected motion. As an example, the EMG device 810 may stream data associated with the detected motion. As another example, the EMG device 810 may communicate information associated with the motion (or status thereof) whenever the EMG device 810 detects a motion.

According to various embodiments of the present disclosure, the EMG device 810 may communicate to the HMD terminal 815 information relating to data stored on the EMG device 810. According to various embodiments of the present disclosure, a user 805 may select the type of information to transmit from the EMG device 810 to the HMD terminal 815. For example, the user 805 may select the type of data for which information is to be transmitted from the EMG device 810 to the HMD terminal 815. The user 805 may select to transmit information about music files store on the EMG device 810 from the EMG device 810 to the HMD terminal 815. The user 805 may select to transmit, from the EMG device 810 to the HMD terminal 815, information about most recently played music files, songs characterized as user 805 favorites, songs by a particular artist, most recently added song, and/or the like. According to various embodiments of the present disclosure, selection of the type of information to transmit from the EMG device 810 to the HMD terminal 815 may be made by a motion. For example, the user 805 may select a type of information to transmit from the EMG device 810 to the HMD terminal 815 according to a user motion that corresponds to a preconfigured motion associated with a type of information.

Referring to FIG. 8B, the HMD terminal 815 may display information 820. According to various embodiments of the present disclosure, the HMD terminal 815 may display information 820 transmitted thereto from the EMG device 810. According to various embodiments of the present disclosure, the HMD terminal 815 may display the information 820 in association with the EMG device 810. For example, the HMD terminal 815 may display the information 820 as an augmented reality in relation to the EMG device 810.

As illustrated in FIG. 8B, as a result of the detected motion of the user 805 illustrated in FIG. 8A, the HMD terminal 815 may display the information 820 so as to appear above the EMG device 810. The HMD terminal 815 may display the information 820 so as to appear above the EMG device 810 when the user 805 looks at the EMG device 810.

As illustrated in FIG. 8B, the information 820 may relate to data stored on the EMG device 810. For example, the information 820 may relate to a category 825 (e.g., music library) of data stored on the EMG device 810. The information 820 may further include specific information relating to the various stored on the EMG device 810. As an example, if the type of information 820 corresponds to a music library, then the information 820 may further include song title 830 for songs 830-1, 830-2, 830-3, 830-4, and 830-5, and detailed song information 835 such as a length of song 835-1, 835-2, 835-3, 835-4, and 835-5 respectively corresponding to songs 830-1 through 830-5.

FIGS. 9A, 9B, 9C, 9D, and 9E are illustrations of an EMG device used in conjunction with an electronic device according to various embodiments of the present disclosure.

Referring to FIG. 9A, a user 905 uses an EMG device 910 in conjunction with at least one electronic device. For example, according to various embodiments of the present disclosure, the user 905 may use the EMG device 910 in conjunction with at least one of an HMD terminal 915 and a mobile terminal 920.

According to various embodiments of the present disclosure, the EMG device 910 may be an armband, a wristwatch, and/or the like.

According to various embodiments of the present disclosure, the EMG device 910 may operatively communicate with the HMD terminal 915. For example, the EMG device 910 may be paired with the HMD terminal 915. As another example, the EMG device 910 may communicate with the HMD terminal 915 through another mobile terminal (e.g., a smartphone, and/or the like) to which both the EMG device 910 and the HMD terminal 915 are connected.

According to various embodiments of the present disclosure, the EMG device 910 may operatively communicate with the source terminal 920. The HMD device 910 may also operatively communicate with the source terminal 920.

According to various embodiments of the present disclosure, the EMG device 910 may detect movement of the user 905. For example, as illustrated in FIG. 9A, the EMG device 910 may detect a grasping motion of the user's 905 hand.

Referring to FIG. 9B, the user 905 may move the user's 905 arm away from source terminal 920. The EMG device 910 may detect movement of the user 905. For example, as illustrated in FIG. 9B, the EMG device 910 may detect a movement of the user's 905 arm (or hand) away from the source terminal 920.

According to various embodiments of the present disclosure, the EMG device 910 may determine that detection of the grasping motion of the user's 905 hand in conjunction with detection of the movement of the user's 905 in relation to the source terminal 920 (e.g., away from the source terminal) corresponds to a request to transfer (e.g., transmit a copy) of data stored on the source terminal 920 to the EMG device 910.

According to various embodiments of the present disclosure, the HMD device 915 may display data being pulled from the source terminal 920. For example, the HMD device 915 may display data associated with the request transmitted by the EMG device 910 for transfer of data from the source terminal 920 to the EMG device 910.

Referring to FIG. 9C, the user terminal 920 may display a UI 925 including a plurality of items (e.g., icons, elements, hyperlinks, shortcuts, files, and/or the like) 925-1 through 925-16.

According to various embodiments of the present disclosure, the EMG device 910 may request transfer of data associated with item 925-1 (or item 925-1 itself) according to the detected motion (e.g., the grasp motion in conjunction with the movement of the user's arm/hand away from the source terminal 920) from the source terminal 920 to the EMG device 910.

According to various embodiments of the present disclosure, the HMD device 915 may display an augmented reality effect in relation to the item 925-1. For example, upon determining (or being operatively informed by at least one of the EMG device 910 and the source terminal 920) that the detected motion relates to item 925-1 (e.g., that the EMG device 910 requests transfer of the item 925-1 from the source terminal 920), the HMD device 915 may display item 925-1 being pulled from UI 925. According to various embodiments of the present disclosure, the augmented reality effect displayed by the HMD device 915 may only be displayed when the user's 905 field of view is directed to the source terminal 920 and/or the user's 905 hand. For example, the HMD device 915 may display an augmented reality effect such that the item 925-1 is pulled from the UI 924 of source terminal 920 and is retained in the user's 905 hand as the user 905 moves the user's 905 hand away from the source terminal 920.

Figure 9D:
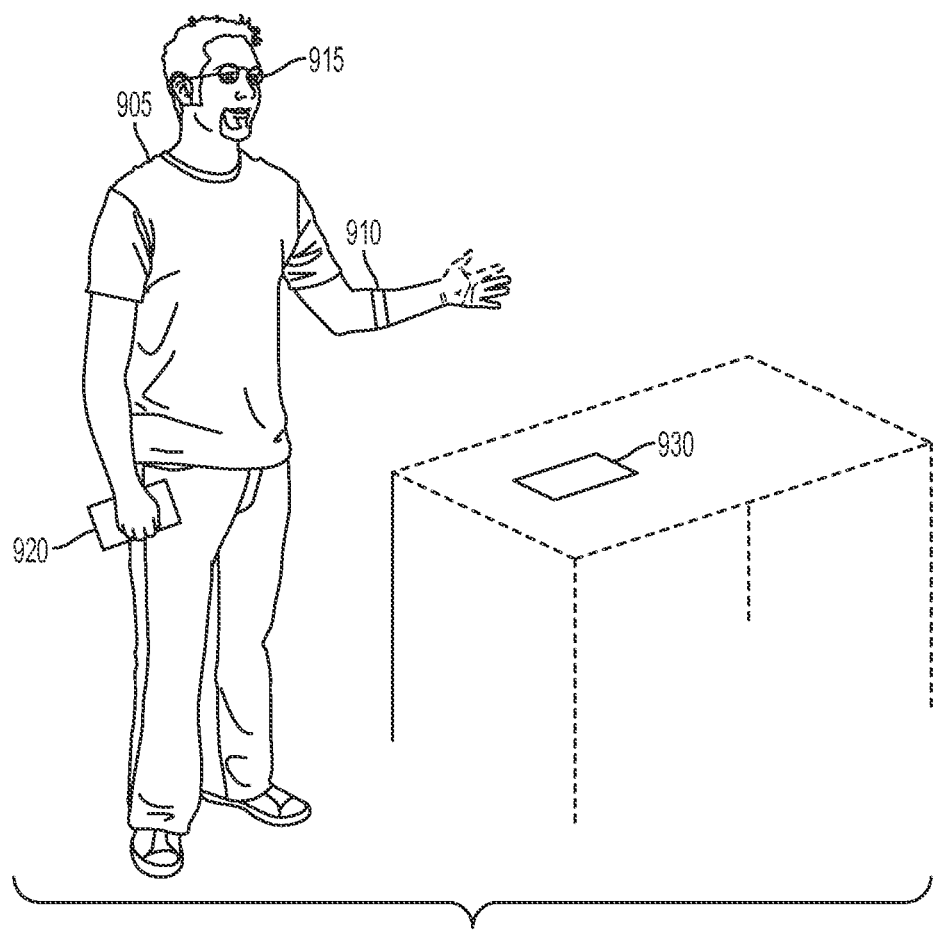
Figure 9E:
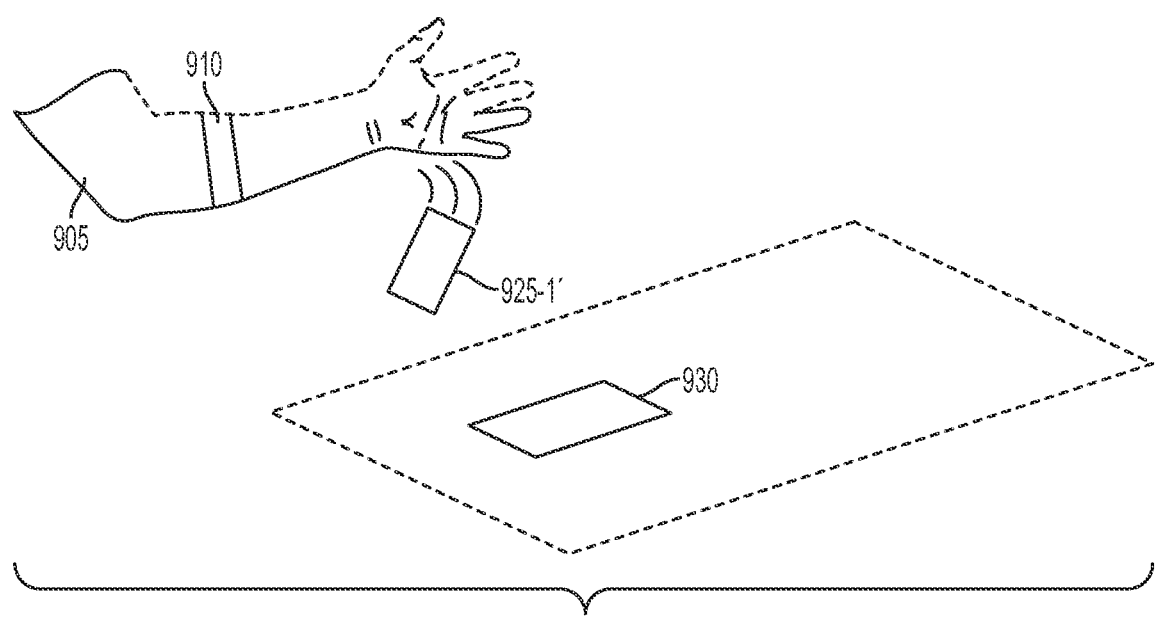

Referring to FIG. 9E, the EMG device 910 may operatively communicate with the target terminal 930. According to various embodiments of the present disclosure, the HMD device 915 and/or the source terminal 920 may also operatively communicate with the target terminal 930.

According to various embodiments of the present disclosure, the EMG device 910 may detect movement of the user 905. For example, as illustrated in FIG. 9D, the EMG device 910 may detect a dropping (or releasing) motion of the user's 905.

According to various embodiments of the present disclosure, the EMG device 910 may determine that detection of the dropping motion of the user's 905 hand corresponds to a request to transfer (e.g., transmit a copy) of data stored on the EMG device 910 to the target terminal 930. For example, the data for which the request to transfer data from the EMG device 910 to the target terminal 930 may correspond to the data transferred from the source terminal 920 to the EMG device 910 as described in relation to FIGS. 9A and 9B. According to various embodiments of the present disclosure, the user 905 may select among all or a subset of data stored on the EMG device 910 to choose the data to be transferred from the EMG device 910 to the target terminal 930.

Referring to FIG. 9E, the HMD device 915 may display data being dropped to the target terminal 930. For example, the HMD device 915 may display data associated with the transfer of data from the EMG device 910 to the target terminal 930. The HMD device 915 may display an augmented reality effect according to which a representation 925-1' of data being transferred from the EMG device 910 to the target terminal 930 is displayed as dropping from the user's 905 hand to the target terminal 930.

It will be appreciated that various embodiments of the present disclosure according to the claims and description in the specification can be realized in the form of hardware, software or a combination of hardware and software.

Any such software may be stored in a non-transitory computer readable storage medium. The non-transitory computer readable storage medium stores one or more programs (software modules), the one or more programs comprising instructions, which when executed by one or more processors in an electronic device, cause the electronic device to perform a method of the present disclosure.

Any such software may be stored in the form of volatile or non-volatile storage such as, for example, a storage device like a Read Only Memory (ROM), whether erasable or rewritable or not, or in the form of memory such as, for example, Random Access Memory (RAM), memory chips, device or integrated circuits or on an optically or magnetically readable medium such as, for example, a Compact Disk (CD), Digital Versatile Disc (DVD), magnetic disk or magnetic tape or the like. It will be appreciated that the storage devices and storage media are various embodiments of non-transitory machine-readable storage that are suitable for storing a program or programs comprising instructions that, when executed, implement various embodiments of the present disclosure. Accordingly, various embodiments provide a program comprising code for implementing apparatus or a method as claimed in any one of the claims of this specification and a non-transitory machine-readable storage storing such a program.

While the disclosure has been shown and described with reference to various embodiments thereof, it will be understood by those skilled in the art that various changes in form and details may be made therein without departing from the spirit and scope of the disclosure as defined by the appended claims and their equivalents.

What is claimed is:

1. A method for transferring data from a source terminal to an Electromyography (EMG) device, the method comprising:
  receiving from a sensor using at least one processor of the EMG device, sensor data based on detected electric signals corresponding to a motion of an arm, a hand, or a finger;
  establishing a connection with the source terminal via a transceiver of the EMG device when the source terminal is within a predetermined distance from the EMG device, the predetermined distance based on an indication that a signal strength of the source terminal is above a threshold;
  determining whether the sensor data indicating the motion matches, within a first predefined confidence interval, a first motion of a plurality of motions, the first motion indicating a request to transfer data between the source terminal and the EMG device;
  in response to determining that the sensor data indicating the motion matches the first motion, transmitting to the source terminal a first message requesting set of data from the source terminal, wherein the set of data is identified by a user of the source terminal according to a first input operatively input to the source terminal;
  after transmitting the first message, receiving from the source terminal the set of data transmitted by the source terminal; and
  reproducing at least a portion of the set of data via a display;
  wherein the connection is established with the source terminal based on a gesture detected at the source terminal.

2. The method of claim 1, further comprising:
  determining whether the sensor data indicating the motion matches, within a second predefined confidence interval, a second motion of the plurality of motions; and
  in response to determining that the sensor data indicating the motion matches the second motion, reproducing, by the EMG device, the set of data according to the second motion.

3. The method of claim 2, wherein the reproducing of the set of data according to the second motion comprises:
  playing back the set of data when the data corresponds to media content.

4. The method of claim 2, wherein the reproducing of the set of data according to the second motion comprises:
  displaying the set of data on a screen operatively connected to the EMG device.

5. The method of claim 1, further comprising:
  determining whether the sensor data indicating the motion matches, within a second predefined confidence interval, a second motion of the plurality of motions;
  determining whether the second motion corresponds to a preconfigured function; and
  in response to determining that the second motion corresponds to the preconfigured function, performing the preconfigured function.

6. The method of claim 5, wherein, when the preconfigured function corresponds to a function for transferring a second set of data from the EMG device to a target terminal, the method further comprises:
  transferring the second set of data to the target terminal, wherein the second set of data is identified by the user of the source terminal according to a second input operatively input to the source terminal.

7. The method of claim 6, wherein the second motion is a drop motion.

8. The method of claim 5, wherein, when the preconfigured function corresponds to a function for deleting specific data, the method further comprises:
deleting the specific data from the EMG device.

9. The method of claim 1, wherein the first motion is a grasp motion.

10. An Electromyography (EMG) device, the EMG device comprising:
a display;
a sensor configured to detect electric signals corresponding to a motion of an arm, a hand, or a finger;
a transceiver; and
at least one processor operably coupled to the display, the sensor, and the transceiver and configured to:
receive sensor data corresponding to the electric signals from the sensor, the sensor data indicating the motion,
establish a connection with a source terminal when the source terminal is within a predetermined distance from the EMG device, the predetermined distance based on an indication that a signal strength of the source terminal is above a threshold,
determine whether the sensor data indicating the motion matches, within a first predefined confidence interval, a first motion of a plurality of motions, the first motion indicating a request to transfer data between the source terminal and the EMG device,
in response to determining that the sensor data indicating the motion matches the first motion, operatively transmit to the source terminal a first message requesting a set of data from the source terminal, wherein the set of data is identified by a user of the source terminal according to a first input operatively input to the source terminal,
after transmitting the first message, receive from the source terminal the set of data transmitted by the source terminal, and
reproduce at least a portion of the set of data via the display,
wherein the connection is established with the source terminal based on a gesture detected at the source terminal.

11. The EMG device of claim 10, wherein the at least one processor is further configured to:
determine whether the sensor data indicating the motion matches, within a second predefined confidence interval, a second motion of the plurality of motions, and
in response to determining that the sensor data indicating the motion matches the second motion, reproduce the set of data on the display of the EMG device according to the second motion.

12. The EMG device of claim 11, wherein:
the set of data is media content; and
to reproduce the set of data, the at least one processor is configured to play the set of data.

13. The EMG device of claim 10, wherein the at least one processor is further configured to:
determine whether the sensor data indicating the motion matches, within a second predefined confidence interval, a second motion of the plurality of motions,
determine whether the second motion corresponds to a preconfigured function, and
in response to determining that the second motion corresponds to the preconfigured function, perform the preconfigured function.

14. The EMG device of claim 13, wherein, when the preconfigured function corresponds to transferring a second set of data from the EMG device to a target terminal, the at least one processor is further configured to operatively transfer the second set of data to the target terminal, and wherein the second set of data is identified by the user of the source terminal according to a second input operatively input to the source terminal.

15. The EMG device of claim 14, wherein the second motion is a drop motion.

16. The EMG device of claim 13, wherein, when the preconfigured function corresponds to deleting specific data, the at least one processor is configured to delete the specific data from the EMG device.

17. The EMG device of claim 10, wherein the first motion is a grasp motion.

18. The EMG device of claim 10, wherein, the sensor is configured to detect muscle activity.

19. The EMG device of claim 18, wherein the sensor comprises at least one EMG muscle sensor configured to measure the muscle activity.

20. A system for transferring data comprising:
an Electromyography (EMG) device; and
a source terminal;
wherein the EMG device comprises:
a display;
a sensor configured to detect electric signals corresponding to a motion of an arm, a hand, or a finger;
a transceiver; and
at least one processor operably coupled to the display, the sensor, and the transceiver and configured to:
receive sensor data corresponding to the electric signals from the sensor, the sensor data indicating the motion;
establish a connection with the source terminal when the source terminal is within a predetermined distance from the EMG device, the predetermined distance based on an indication that a signal strength of the source terminal is above a threshold;
determine whether the sensor data indicating the motion matches, within a first predefined confidence interval, a first motion of a plurality of motions, the first motion indicating a request to transfer data between the source terminal and the EMG device;
in response to determining that the sensor data indicating the motion matches the first motion, operatively transmit to the source terminal a first message requesting a set of data from the source terminal, wherein the set of data is identified by a user of the source terminal according to a first input operatively input to the source terminal;
after transmitting the first message, receive from the source terminal the set of data transmitted by the source terminal; and
reproduce at least a portion of the set of data via the display; and
wherein the source terminal comprises:
a memory configured to store data;
a second transceiver configured to communicate with the EMG device; and at least one second processor configured to receive the request to transfer data and to operatively transmit to the EMG device the set of data associated with the request.

21. The system of claim 20, wherein the at least one processor of the EMG device is further configured to:
   determine whether the sensor data indicating the motion matches, within a second predefined confidence interval, a second motion of the plurality of motions;
   determine whether the second motion corresponds to a preconfigured function, and
   perform the preconfigured function in response to determining that the second motion corresponds to the preconfigured function.

22. The system of claim 21, further comprising:
   a target terminal comprising:
      a second memory configured to store data;
      a third transceiver configured to communicate with the EMG device; and
      at least one third processor configured to receive data from the EMG device according to a user motion detected by the EMG device and to operatively store the data,
   wherein, when the preconfigured function corresponds to a function for transferring a second set of data from the EMG device to the target terminal, the EMG device is configured to transfer the second set of data to the target terminal.

23. A non-transitory computer-readable storage medium storing instructions that, when executed, cause at least one processor of an Electromyography (EMG) device to:
   receive, from a sensor, sensor data based on detected electric signals corresponding to a motion of an arm, a hand, or a finger;
   establish a connection with a source terminal via a transceiver when the source terminal is within a predetermined distance from the EMG device, the predetermined distance based on an indication that a signal strength of the source terminal is above a threshold;
   determine whether the sensor data indicating the motion matches, within a first predefined confidence interval, a first motion of a plurality of motions, the first motion indicating a request to transfer data between the source terminal and the EMG device;
   in response to determining that the sensor data indicating the motion matches the first motion, transmit to the source terminal a first message requesting a set of data from the source terminal, wherein the set of data is identified by a user of the source terminal according to a first input operatively input to the source terminal;
   after transmitting the first message, receive from the source terminal the set of data transmitted by the source terminal; and
   reproduce at least a portion of the set of data via a display of the EMG device;
   wherein the connection is established with the source terminal based on a gesture detected at the source terminal.

24. The non-transitory computer-readable storage medium of claim 23, further storing instructions that, when cured, cause the at least one processor to:
   determine whether the sensor data indicating the motion matches, within a second predefined confidence interval, a second motion of the plurality of motions, and
   in response to determining that the sensor data indicating the motion matches the second motion, reproduce the set of data on the display of the EMG device according to the second motion.

25. The non-transitory computer-readable storage medium of claim 23, further storing instructions that, when executed, cause the at least one processor to:
   determine whether the sensor data indicating the motion matches, within a second predefined confidence interval, a second motion of the plurality of motions,
   determine whether the second motion corresponds to a preconfigured function, and
   in response to determining that the second motion corresponds to the preconfigured function, perform the preconfigured function.

26. The non-transitory computer-readable storage medium of claim 25, further storing instructions that, when executed, cause the at least one processor, when the preconfigured function corresponds to a function for transferring a second set of data from the EMG device to a target terminal, to:
   transfer the second set of data to the target terminal, wherein the second set of data is identified by the user of the source terminal according to a second input operatively input to the source terminal.

27. The non-transitory computer-readable storage medium of claim 25, further storing instructions that, when executed, cause the at least one processor, when the preconfigured function corresponds to a function for deleting specific data, to:
   delete the specific data from the EMG device.

* * * * *